(12) United States Patent
Cha et al.

(10) Patent No.: US 11,426,869 B2
(45) Date of Patent: Aug. 30, 2022

(54) END EFFECTOR OF SURGICAL ROBOT

(71) Applicant: CUREXO, INC., Seoul (KR)

(72) Inventors: Yong Yeob Cha, Seoul (KR); Seung Jae Ryu, Gwangmyeong-si (KR); Hong Ho Kim, Daejeon (KR)

(73) Assignee: CUREXO, INC., Seoul (KR)

( * ) Notice: Subject to any disclaimer, the term of this patent is extended or adjusted under 35 U.S.C. 154(b) by 0 days.

(21) Appl. No.: 17/437,655

(22) PCT Filed: Mar. 13, 2020

(86) PCT No.: PCT/KR2020/003528
§ 371 (c)(1),
(2) Date: Sep. 9, 2021

(87) PCT Pub. No.: WO2020/185031
PCT Pub. Date: Sep. 17, 2020

(65) Prior Publication Data
US 2022/0040855 A1    Feb. 10, 2022

(30) Foreign Application Priority Data
Mar. 13, 2019 (KR) .................. 10-2019-0028623

(51) Int. Cl.
 *B25J 9/16* (2006.01)
 *A61B 34/20* (2016.01)
 *A61B 34/30* (2016.01)

(52) U.S. Cl.
 CPC .......... *B25J 9/1633* (2013.01); *A61B 34/20* (2016.02); *A61B 34/30* (2016.02); *A61B 2034/2055* (2016.02)

(58) Field of Classification Search
None
See application file for complete search history.

(56) References Cited

U.S. PATENT DOCUMENTS

| 8,672,922 B2* | 3/2014 | Loh ..................... A61B 34/30 606/1 |
| 11,129,681 B2* | 9/2021 | Amiot ................. A61B 34/10 |
| 2006/0095022 A1* | 5/2006 | Moll .................... A61B 46/10 606/1 |

(Continued)

FOREIGN PATENT DOCUMENTS

| KR | 10-2011-0030038 A | 3/2011 |
| KR | 10-1234618 B1 | 2/2013 |

(Continued)

*Primary Examiner* — Carl H Layno
*Assistant Examiner* — Manolis Pahakis
(74) *Attorney, Agent, or Firm* — Novick, Kim & Lee, PLLC; Jae Youn Kim; Jihun Kim

(57) ABSTRACT

An end effector of a surgical robot, including a force/torque sensor module mounted to a robot arm, an end effector frame to which the force/torque sensor module is coupled, a clamping unit installed in the end effector frame, and a tool mounting unit detachably coupled to the end effector frame by the clamping unit and supporting a surgical tool. The end effector can help to rapidly and conveniently perform a surgical operation by the robot, thereby not only safely carrying out a surgical process but also easily and accurately gripping a surgical tool during the surgical operation and setting and keeping a location of the surgical tool and a surgical site.

7 Claims, 10 Drawing Sheets

(56) References Cited

U.S. PATENT DOCUMENTS

| | | | | |
|---|---|---|---|---|
| 2006/0142657 A1* | 6/2006 | Quaid | ................ | A61F 2/30942 |
| | | | | 600/424 |
| 2006/0161136 A1* | 7/2006 | Anderson | .............. | A61B 34/71 |
| | | | | 606/1 |
| 2007/0270685 A1* | 11/2007 | Kang | ..................... | A61B 34/20 |
| | | | | 600/424 |
| 2008/0009697 A1* | 1/2008 | Haider | ................... | G16H 40/63 |
| | | | | 600/407 |
| 2011/0106102 A1* | 5/2011 | Balicki | ................ | A61B 3/1005 |
| | | | | 606/1 |
| 2011/0282351 A1 | 11/2011 | Holop et al. | | |
| 2012/0265051 A1* | 10/2012 | Fischer | .............. | A61B 10/0241 |
| | | | | 73/800 |
| 2013/0066304 A1* | 3/2013 | Belson | ..................... | A61B 1/32 |
| | | | | 606/1 |
| 2013/0345718 A1* | 12/2013 | Crawford | ............... | A61B 90/14 |
| | | | | 606/130 |
| 2014/0194699 A1* | 7/2014 | Roh | ....................... | A61B 90/13 |
| | | | | 600/249 |
| 2015/0063936 A1* | 3/2015 | Azzarello | ............... | B23P 23/02 |
| | | | | 409/132 |
| 2016/0113728 A1* | 4/2016 | Piron | ....................... | A61B 5/06 |
| | | | | 606/130 |
| 2016/0361125 A1* | 12/2016 | Balicki | .................. | A61B 34/30 |
| 2017/0086927 A1* | 3/2017 | Auld | ...................... | A61B 34/30 |
| 2017/0135771 A1* | 5/2017 | Auld | ...................... | A61B 34/37 |
| 2017/0143429 A1* | 5/2017 | Richmond | ............ | A61B 90/361 |
| 2017/0202607 A1* | 7/2017 | Shelton, IV | ... | A61B 17/320092 |
| 2017/0348061 A1* | 12/2017 | Joshi | ...................... | A61B 34/20 |
| 2018/0021097 A1 | 1/2018 | Rony et al. | | |
| 2018/0267690 A1* | 9/2018 | Kemp | .................... | B25J 9/1689 |
| 2018/0325608 A1* | 11/2018 | Kang | ..................... | A61B 34/71 |
| 2018/0325609 A1* | 11/2018 | Kostrzewski | .......... | A61B 34/30 |
| 2019/0053863 A1* | 2/2019 | Hongo | .................. | B25J 9/1065 |
| 2019/0090966 A1* | 3/2019 | Kang | ................. | A61B 17/8875 |
| 2019/0142543 A1* | 5/2019 | Cha | .......................... | A61B 6/03 |
| | | | | 600/429 |
| 2019/0175272 A1* | 6/2019 | Khan | .................. | A61B 18/203 |
| 2019/0228859 A1* | 7/2019 | Moctezuma de la Barrera | .......... | |
| | | | | G06K 9/00 |

FOREIGN PATENT DOCUMENTS

| | | |
|---|---|---|
| KR | 10-2013-0137128 A | 12/2013 |
| KR | 10-2016-0051043 A | 5/2016 |
| KR | 10-1911843 B1 | 10/2018 |
| WO | 12/018816 A2 | 2/2012 |
| WO | WO-2017222274 A2 * | 12/2017 ......... A61B 10/0233 |

\* cited by examiner

END EFFECTOR OF SURGICAL ROBOT

CROSS-REFERENCE TO RELATED APPLICATIONS

This application is a national stage application, filed under 35 U.S.C. § 371, of International Patent Application No. PCT/KR2020/003528, filed on Mar. 13, 2020, which is incorporated by reference herein in its entirety, and additionally claims priority from Korean Patent Application No. 10-2019-0028623, filed on Mar. 13, 2019, which is also incorporated herein by reference in its entirety.

TECHNICAL FIELD

The disclosure relates to an end effector of a surgical robot, and more particularly to an end effector of a surgical robot, which can rapidly and conveniently perform a surgical operation by the robot, thereby not only safely carrying out a surgical process but also easily and accurately gripping a surgical tool during the surgical operation and setting and keeping a location of the surgical tool and a surgical site.

BACKGROUND ART

In general, a surgical robot refers to a medical robot that assists a medical doctor in performing a surgical operation, and a robot-based surgery method has been in the limelight because a patient recovers quickly and the surgical operation is accurately performed with an optimized removal part. Further, such a surgical robot has been developed and widely used as a surgery method with advancement of medical technology.

At present, the surgical robot has been developed and used as a laparoscopic surgery robot that operates on prostate, stomach, heart and the like soft tissue; an artificial-joint surgery robot that operates on a knee joint and the like hard tissue; a vascular surgery robot that operates as inserted in a blood vessel through a catheter or the like; etc.

Besides, the surgical robot has been used as a robot for intervention, etc. with an end effector, which performs medical and surgical operations such as tissue biopsy, dilation, drug injection, etc. by inserting a medical instrument into a human body while observing the inside of the human body through an imaging device.

Recently, the surgical robot has also been researched and developed to be used even in spinal surgery, such as correcting a position of a spine by inserting a fixing device for pedicle fixation, relieving a compressed nerve, etc.

For example, a pedicle screw insertion surgery, which is one of representative spine surgeries, is to perform spinal fusion by inserting a pedicle screw into a plurality of pedicles, and coupling the pedicle screw and an adjacent pedicle screw by a rod, so that the spines can be corrected to widen a distance between a pedicle compressing a nerve and an adjacent pedicle, thereby preventing the pedicle from compressing the nerve.

The pedicle screw insertion surgery is carried out in such a manner that the pedicle screw is inserted into a plurality of pedicles by a fastening tool, which is called a driver, and then the screw heads of the pedicle screws are coupled by the rod. However, when the pedicle screw insertion surgery is performed by medical personnel, about 12 or more surgical steps are needed and a lot of tools and procedures are required until the pedicle screw is inserted into the pedicle, and thus there is a disadvantage of a very complicated surgical process.

Further, the pedicle screw insertion surgery has disadvantages that it is very difficult to accurately and stably perform the surgical operation and it takes too much time to carry out the surgical operation because gripping of a surgical tool, setting and keeping of a location of the surgical tool and a surgical site, etc. rely upon handwork of medical personnel.

Further, the conventional pedicle screw insertion surgery has a disadvantage of increasing radiation exposure to a patient or medical staff because repetitive radiography is involved in a process of inserting the surgical tool, etc.

Accordingly, there is urgently required an end effector, which can perform not only the spine surgery using the surgical robot but also grip a surgical tool, set and keep the location of the surgical tool and the surgical site, etc. during the spine surgery as easily mounted to the robot arm without relying upon handwork of medical personnel.

DISCLOSURE

Technical Problem

Accordingly, the disclosure is conceived based on the foregoing disadvantages, and an aspect of the disclosure is to provide an end effector of a surgical robot, which not only quickly and easily performs a surgical operation but also safely carries out the surgical process by the robot.

Another aspect of the disclosure is to provide an end effector of a surgical robot, which easily and accurately perform gripping a surgical tool during a surgical operation, setting and keeping a location of the surgical tool and a surgical site, etc.

Technical Solution

According to an aspect of the disclosure, there is provided an end effector of a surgical robot, including: a force/torque sensor module mounted to a robot arm; an end effector frame to which the force/torque sensor module is coupled; a clamping unit installed in the end effector frame; and a tool mounting unit detachably coupled to the end effector frame by the clamping unit and supporting a surgical tool.

The tool mounting unit may include: a mounting bar including a first end connected to the end effector frame and a second end formed with a tool supporter; a tool guide member installed in the tool supporter and supporting the surgical tool; and a tool presence detector installed in the mounting bar and configured to detect presence of the tool guide member.

Here, the tool supporter may include a supporting body curvedly formed in a lower end of the mounting bar body in a horizontal direction, and a guide hole formed in the supporting body in up and down directions and including an opening formed at one side.

The mounting bar may include a mounting bar body formed with the tool supporter in a lower end thereof and internally provided with the tool presence detector; a mounting bar cover coupled to the mounting bar body and including a second terminal to be connected to a first terminal provided in the end effector frame; and a mounting bar coupler coupled to an upper end of the mounting bar body and installed with the clamping unit.

The tool guide member may include an insertion portion inserted in the guide hold and formed with a hanging groove recessed on an outer surface thereof; and a hanging ring formed in an upper end of the insertion portion and hung on the supporting body.

Further, the tool mounting unit may include a guide member stopper is formed in the mounting bar body and elastically settled in the hanging groove.

In addition, the clamping unit may include a first clamping unit installed in the end effector frame; and a second clamping unit installed in the tool mounting unit and detachably coupled to the first clamping unit.

The end effector of the surgical robot may further include an end effector case installed to surround an outside of the end effector frame, and a line laser installed in the end effector frame and generating a laser beam for marking a surgical site, and the end effector case may include a pair of beam emission slits obliquely formed to emit the laser beam generated in the line laser to an outside.

The end effector frame may include a sensor module mounting portion to which the force/torque sensor module is mounted; a clamp mounting portion to which the first clamping unit is mounted, and a case holding bracket to which the end effector case is coupled.

Further, a drape adapter may be installed between the first clamping unit and the second clamping unit to hold a sterilized cloth.

The drape adapter may include a sterilized cloth holder interposed between the first clamping unit and the second clamping unit and holding a sterilized cloth; and a light transmissive portion formed in the sterilized cloth holder and facing the beam emission slit.

The tool mounting unit may include a marker member installed to provide an optical signal to an optical tracking system to track a location of the end effector.

Advantageous Effects

With the end effector of the surgical robot according to the disclosure, the detachable tool mounting unit is convenient to prepare for a surgical operation, the sterilized cloth is easily installed to isolate a sterilized area and a non-sterilized area, and the line laser is used to quickly and accurately mark a surgical site, so that not only a robot-based surgical operation can be rapidly performed but also setting and keeping a location of a surgical tool and a surgical site, etc. are easily and accurately carried out, thereby having effects on enhancing accuracy in the surgical operation.

Further, with the end effector of the surgical robot according to the disclosure, the tool presence detector provided in the tool mounting unit detects the installed state of the surgical tool and it is thus possible to identify whether the surgical operation is proceeding. Therefore, when the mounted state of the surgical tool is detected, the actuation of the robot is prevented, thereby preventing a medical accident due to malfunction of the robot. Further, the tool supporter is formed with the opening, so that the surgical tool can easily pass through the opening even in a state that the pedicle screw is installed in the surgical tool during the pedicle screw insertion surgery, thereby having an advantage of smoothly performing a surgical process.

DESCRIPTION OF DRAWINGS

FIGS. 9A to 9C are views for describing operations of an end effector of a surgical robot according to an embodiment of the disclosure, in which FIG. 9A shows a state before the tool mounting unit is mounted, FIG. 9B shows a state that a sterilized cloth and a tool mounting unit are installed and a surgical tool is installed, and FIG. 9C is a perspective view of the surgical tool used in a pedicle screw insertion surgery, which is one of representative spine surgeries.

MODE FOR INVENTION

Below, embodiments of the disclosure will be described with reference to the accompanying drawings of FIGS. 1 to 9C, in which like numerals refer to like elements throughout.

Further, detailed descriptions about elements and their operations and effects, which are easily understood by a person having ordinary knowledge in the art from general technology, in the accompanying drawings will be simplified or omitted. In addition, the disclosure is characterized in an end effector of a surgical robot, and thus illustration and description will be made focusing on related parts while simplifying or omitting the other parts.

Figure 1:
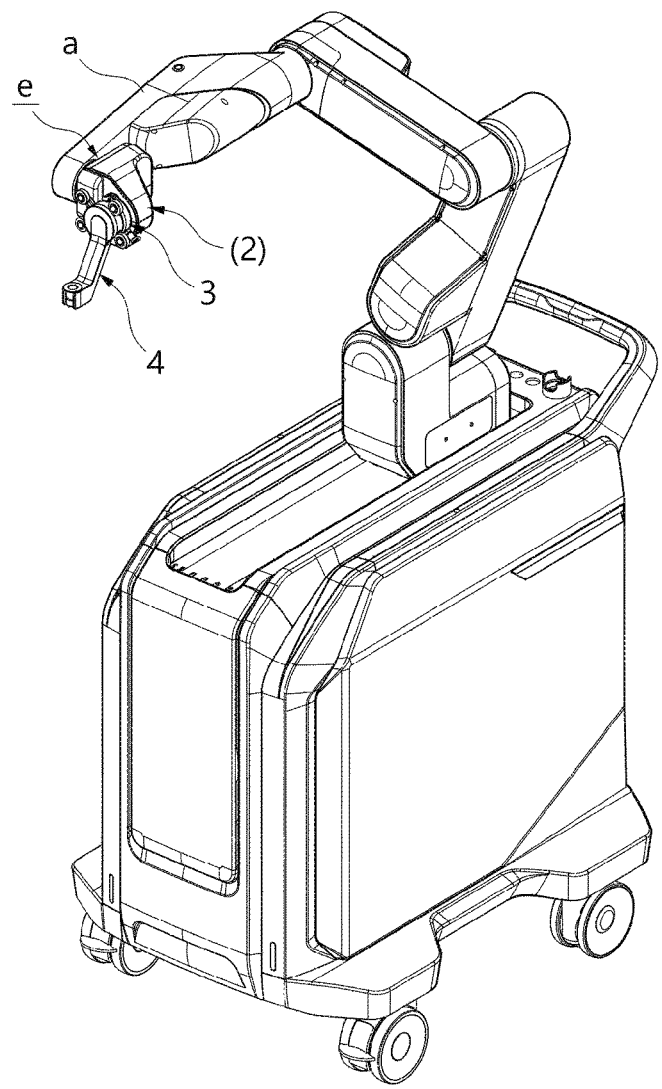
FIG. 1 is a perspective view showing that an end effector is mounted to a surgical robot according to an embodiment of the disclosure.
Figure 2:
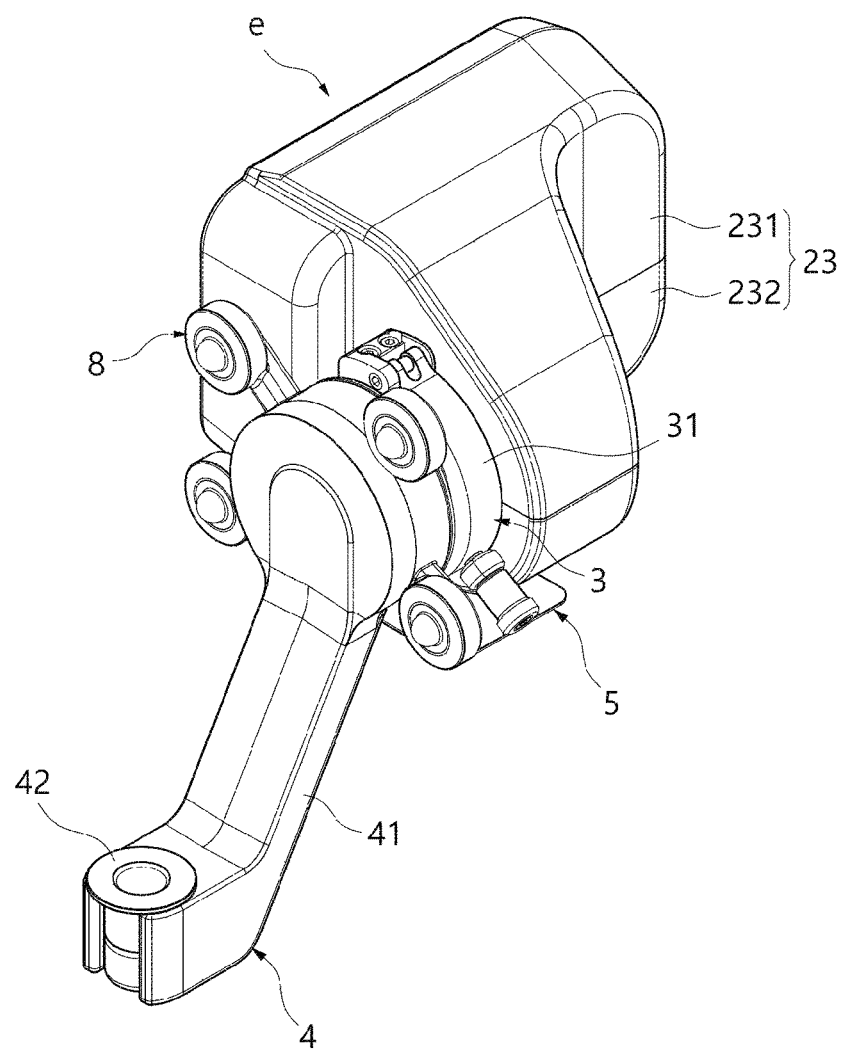
FIG. 2 is an assembled perspective view showing an outer appearance of an end effector of a surgical robot according to an embodiment of the disclosure.
Figure 3:
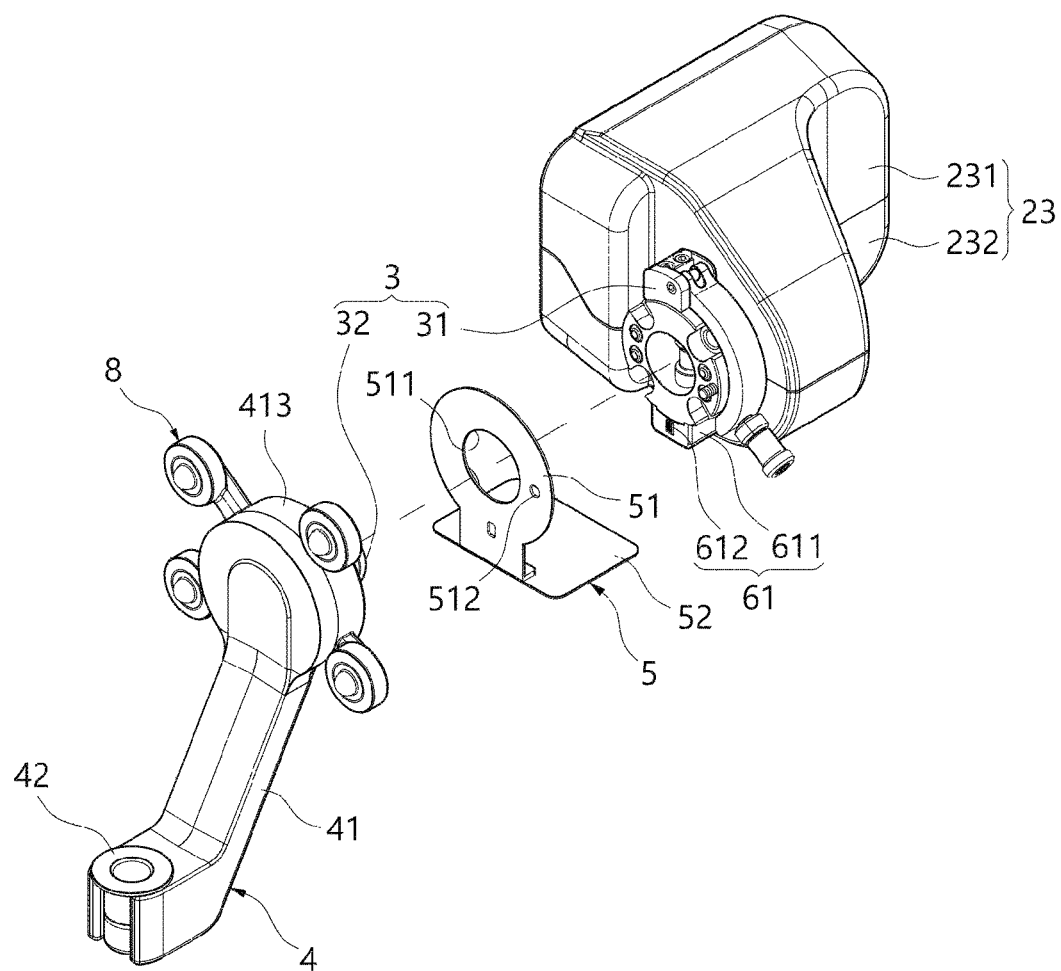
FIG. 3 is a schematically exploded perspective view showing an end effector of a surgical robot according to an embodiment of the disclosure.
Figure 4:
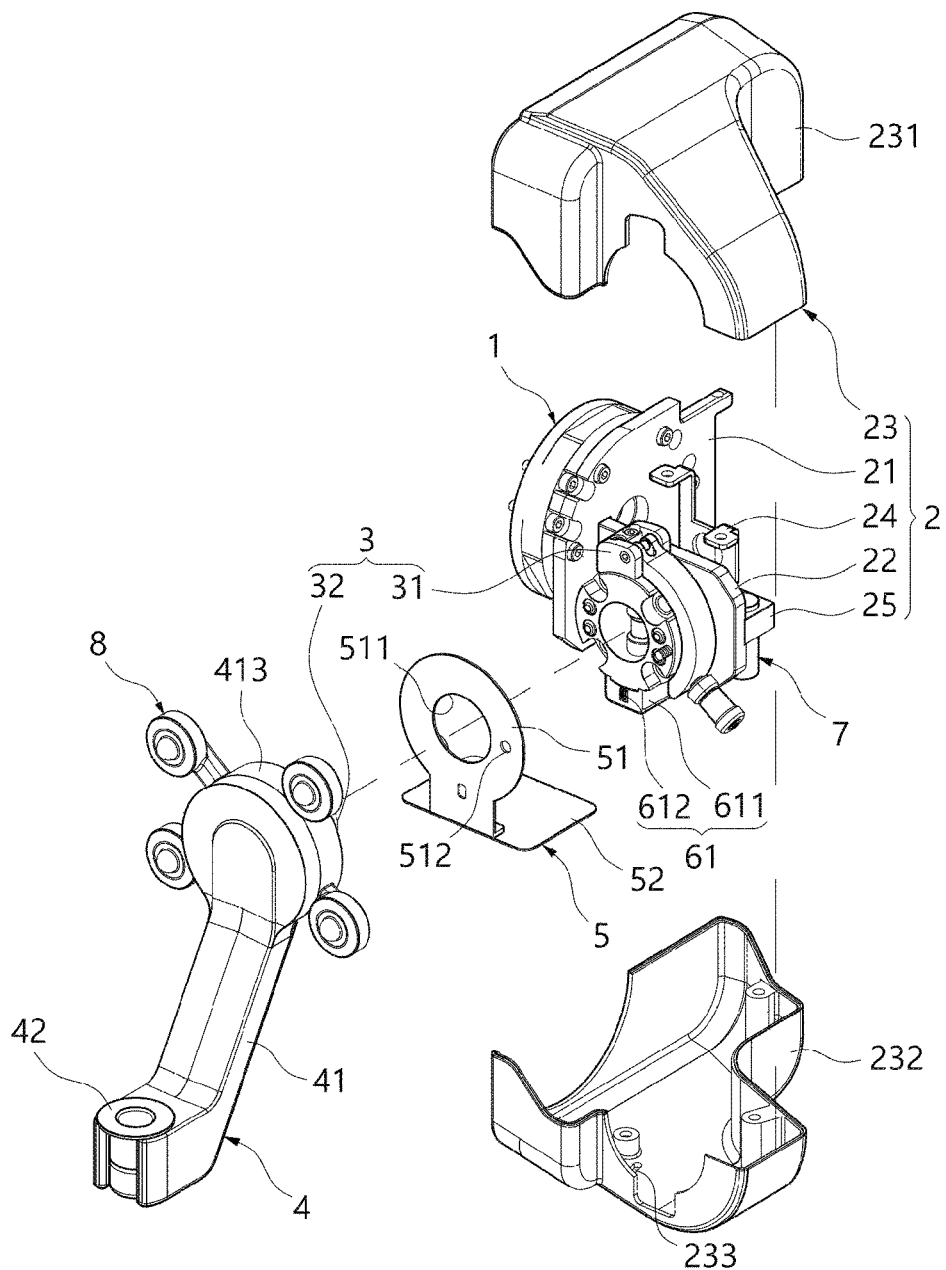
FIG. 4 is an exploded perspective view of a main element in an end effector of a surgical robot according to an embodiment of the disclosure.
Figure 5:
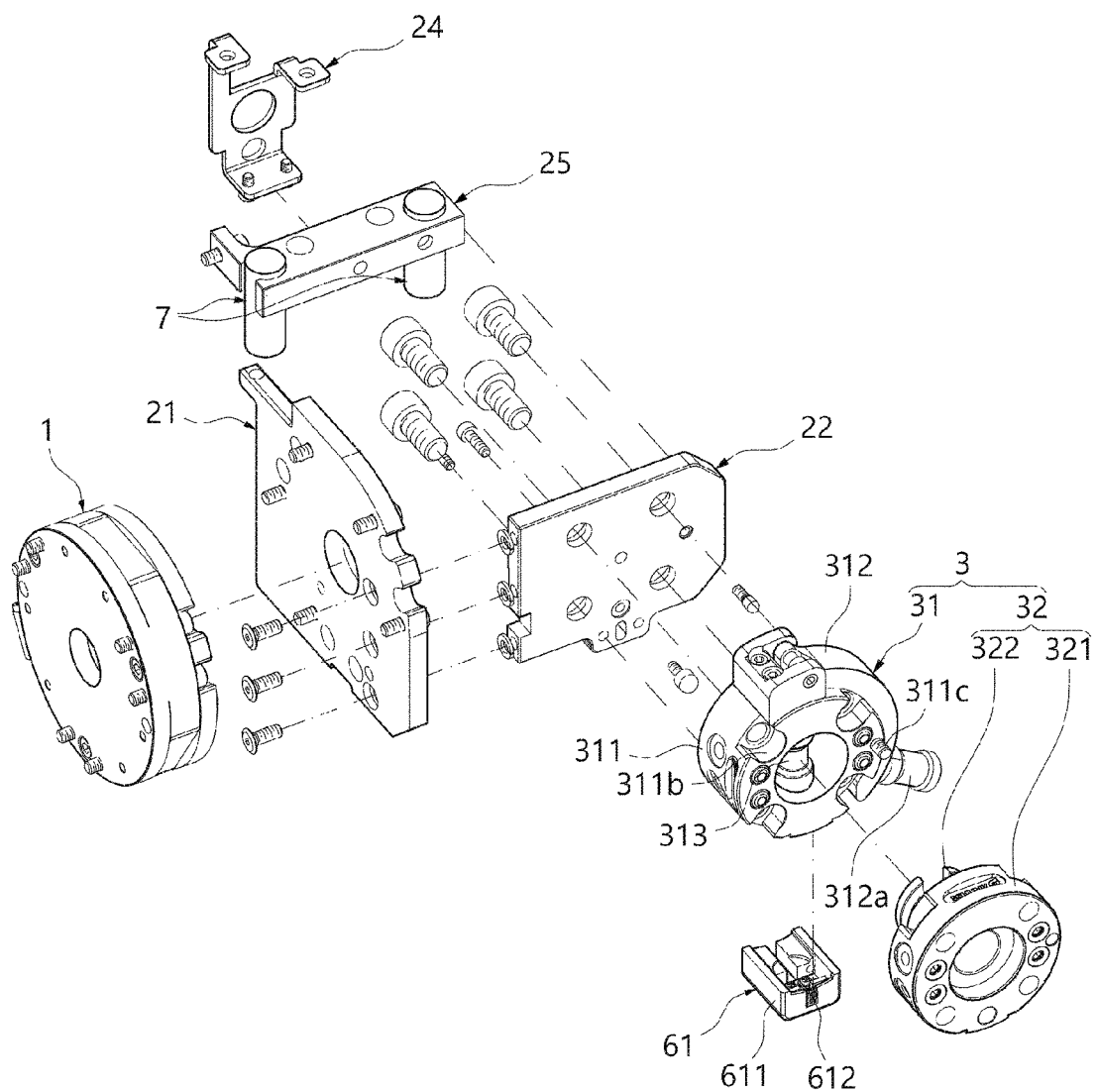
FIG. 5 is an exploded perspective view of an end effector frame in a main element in an end effector of a surgical robot according to an embodiment of the disclosure.

FIG. 1 is a perspective view showing that an end effector is mounted to a surgical robot according to an embodiment of the disclosure, FIG. 2 is an assembled perspective view showing an outer appearance of an end effector of a surgical robot according to an embodiment of the disclosure, FIG. 3 is a schematically exploded perspective view showing an end effector of a surgical robot according to an embodiment of the disclosure, FIG. 4 is an exploded perspective view of a main element in an end effector of a surgical robot according to an embodiment of the disclosure, and FIG. 5 is an exploded perspective view of an end effector frame in a main element in an end effector of a surgical robot according to an embodiment of the disclosure.

Referring to FIGS. 1 to 5, the end effector e of the surgical robot according to an embodiment of the disclosure is configured to grip a surgical tool t during spine surgery, and easily and accurately set and keep a location of the surgical tool and a surgical site, etc., which includes a force/torque sensor module 1, an end effector frame 2, a clamping unit 3, and a tool mounting unit 4. In particular, the end effector of the surgical robot according to an embodiment of the disclosure is configured to easily and safely insert a pedicle screw in a pedicle along a planned path during pedicle screw insertion surgery.

The force/torque sensor module 1 refers to a sensor for measuring external force applied to the end effector and controlling activation of the robot, is typically called an F/T sensor, an overload protecting device, etc., and is mounted to an end of a robot arm a to which the end effector is installed. Further, the force/torque sensor module 1 is a publicly known element, which has been widely used for a medical robot or an industrial robot, and thus descriptions about detailed structures thereof will be omitted.

The end effector frame 2 functions as a main body to which major elements are mounted, and includes a sensor module mounting portion 21 and a clamp mounting portion 22 according to an embodiment. However, there are no specific limits to the structure and shape of the end effector frame 2.

The sensor module mounting portion 21 refers to a portion to which the force/torque sensor module 1 is mounted, and is provided as a plate member formed with a plurality of fastening holes to which fastening members for assembling the force/torque sensor module are fastened.

The clamp mounting portion 22 refers to a portion to which a first clamping unit 31 of the clamping unit 3 is mounted, is assembled in a direction perpendicular to the sensor module mounting portion 21, and is provided as a plate member formed with a plurality of fastening holes to which fastening members for assembling the first clamping unit 31 are fastened.

Further, the clamp mounting portion 22 includes a first terminal 61 electrically connected to a second terminal 62 (to be described later). The first terminal 61 includes a terminal piece 612 installed to be exposed to the outside in a first terminal housing 611 fastened to the clamp mounting portion 22 by the fastening member, and is electrically connected to a terminal piece 621 of the second terminal 62 (to be described later) in a state that the tool mounting unit 4 is mounted to the end effector frame 2.

The end effector frame 2 includes an end effector case 23 for protecting major elements placed therein, and a case holding bracket 24 for holding the end effector case 23.

The end effector case 23 is formed to surround the outside of the end effector frame 2 with a thin plate, includes an upper case 231 and a lower case 232, and is fastened to the case holding bracket 24, etc. by a fastening member.

Figure 6:
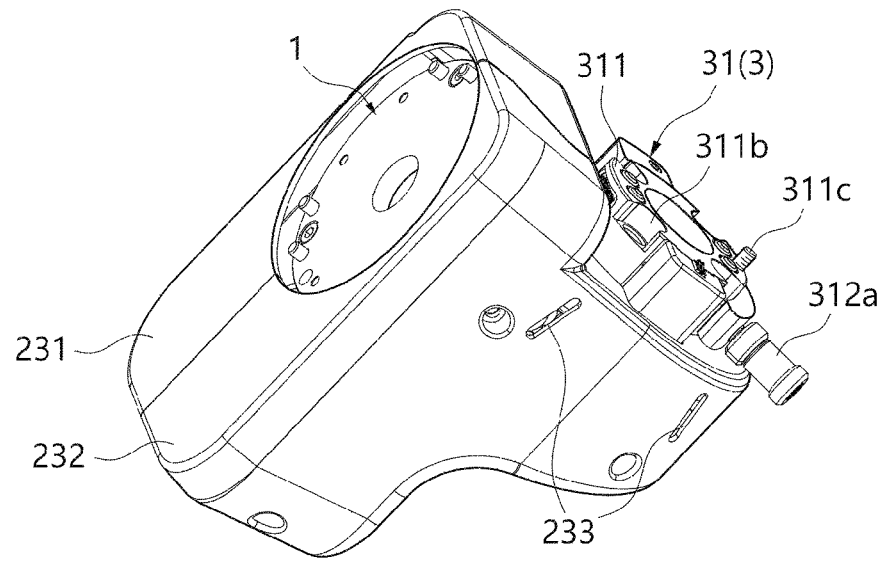
FIG. 6 is a perspective view of an end effector case in an end effector of a surgical robot according to an embodiment of the disclosure.

FIG. 6 is a view for describing an end effector case provided in an end effector of a surgical robot according to an embodiment of the disclosure, in which the bottom of the end effector case is illustrated.

Referring to FIG. 6, the end effector case 23 is formed with a beam emission slit 233 through which a laser beam generated in a line laser 7 (to be described later) is emitted to the outside.

Further, the beam emission slit 233 is formed as a pair of elongated holes formed by obliquely perforating the bottom of the end effector case 23, which are symmetrically structured to have an acute angle for converging on a predetermined vanishing point so that the emitted laser beams can form an intersection for marking a surgical site.

The case holding bracket 24 includes a plurality of fastening portions formed by bending a plate member and having a fastening hole, and is fastened to a laser bracket 25 (to be described later).

Further, the end effector frame 2 includes the line laser 7 for generating the laser beam to mark a surgical site. The line laser 7 is installed in the laser bracket 25 coupled to the clamp mounting portion 22 as shown in FIG. 5.

The line laser 7 includes a built-in laser diode module and the like in a cylindrical body thereof, is configured to emit the laser beam when power is supplied, and includes a light emitter installed in a laser installation hole formed in the laser bracket 25 so as to face toward the beam emission slit 233 of the end effector case 23.

The clamping unit 3 is provided to clamp or separate the tool mounting unit 4 to or from the end effector frame 2, and includes the first clamping unit 31 installed in the end effector frame 2, and a second clamping unit 32 installed in the tool mounting unit 4 and detachably coupled to the first clamping unit 31.

The first clamping unit 31 includes a first clamp body 311 formed with a hollow, a clamp lever 312 rotatably installed in the first clamp body 311 and including a grip 312a, and a clamping shaft 313 moving up and down corresponding to a turning operation of the clamp lever 312 and formed with locking projections.

Further, the first clamp body 311 includes a plurality of locking grooves 311b recessed at a circumferential edge thereof to receive the locking projections 513 of a drape adapter 5 (to be described later), and a location settling pin 311c for settling the locations of parts to assembled.

The second clamping unit 32 includes a second clamp body 321 coupled to a mounting bar (to be described later), and a clamp projection 322 protruding from the second clamp body 321 and formed with a locking hole to be put on or mounted to the clamping shaft 313 the first clamping unit 31.

The foregoing first and second clamping units 31 and 32 may be variously configured without any specific limits to their structures and shapes as long as they allow the tool mounting unit 4 to be detachably mounted.

Figure 7:
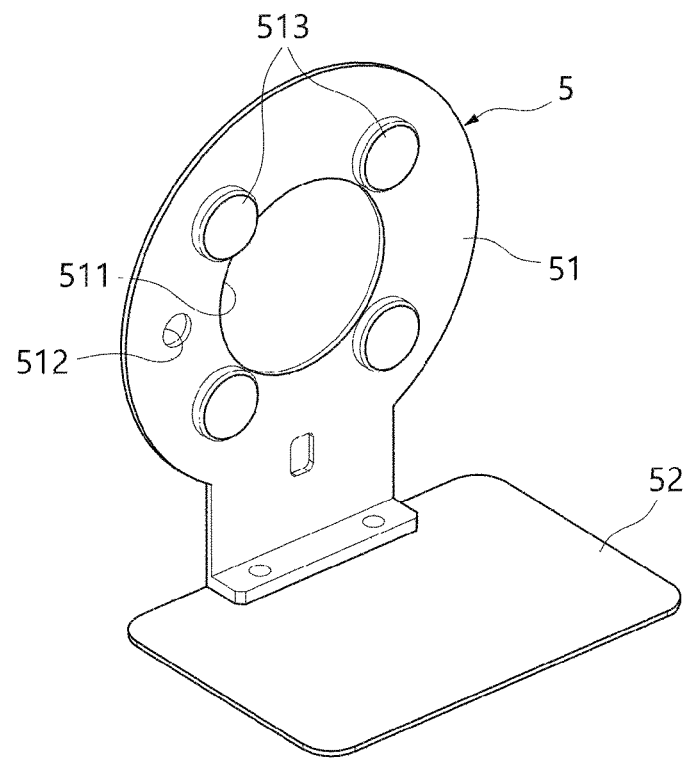
FIG. 7 is a perspective view of a drape adapter in an end effector of a surgical robot according to an embodiment of the disclosure.

FIG. 7 is a perspective view of a drape adapter in an end effector of a surgical robot according to an embodiment of the disclosure.

Referring to FIG. 7, the end effector of the surgical robot according to an embodiment of the disclosure includes the drape adapter 5 between the first clamping unit 31 and the second clamping unit 32 to isolate a sterilized area from a non-sterilized area during a surgical operation.

The drape adapter 5 includes a sterilized cloth holder 51 interposed between the first clamping unit 31 and the second clamping unit 32 and holding a sterilized cloth s, and a light transmissive portion 52 formed in the sterilized cloth holder 51 and facing the beam emission slit 233.

The sterilized cloth holder 51 includes a through hole 511 formed at the center of a thin plate body shaped like an approximately circular plate, a plurality of locking projections 513 protruding from an inner surface thereof around the through hole, and a pin insertion hole 512 in which the location settling pin 311c of the first clamping unit 31 is inserted.

The light transmissive portion 52 is made of polycarbonate (PC) or the like light transmissive plate or sheet excellent in light transmittivity so as to easily transmit the laser beam generated in the line laser 7.

Figure 8:
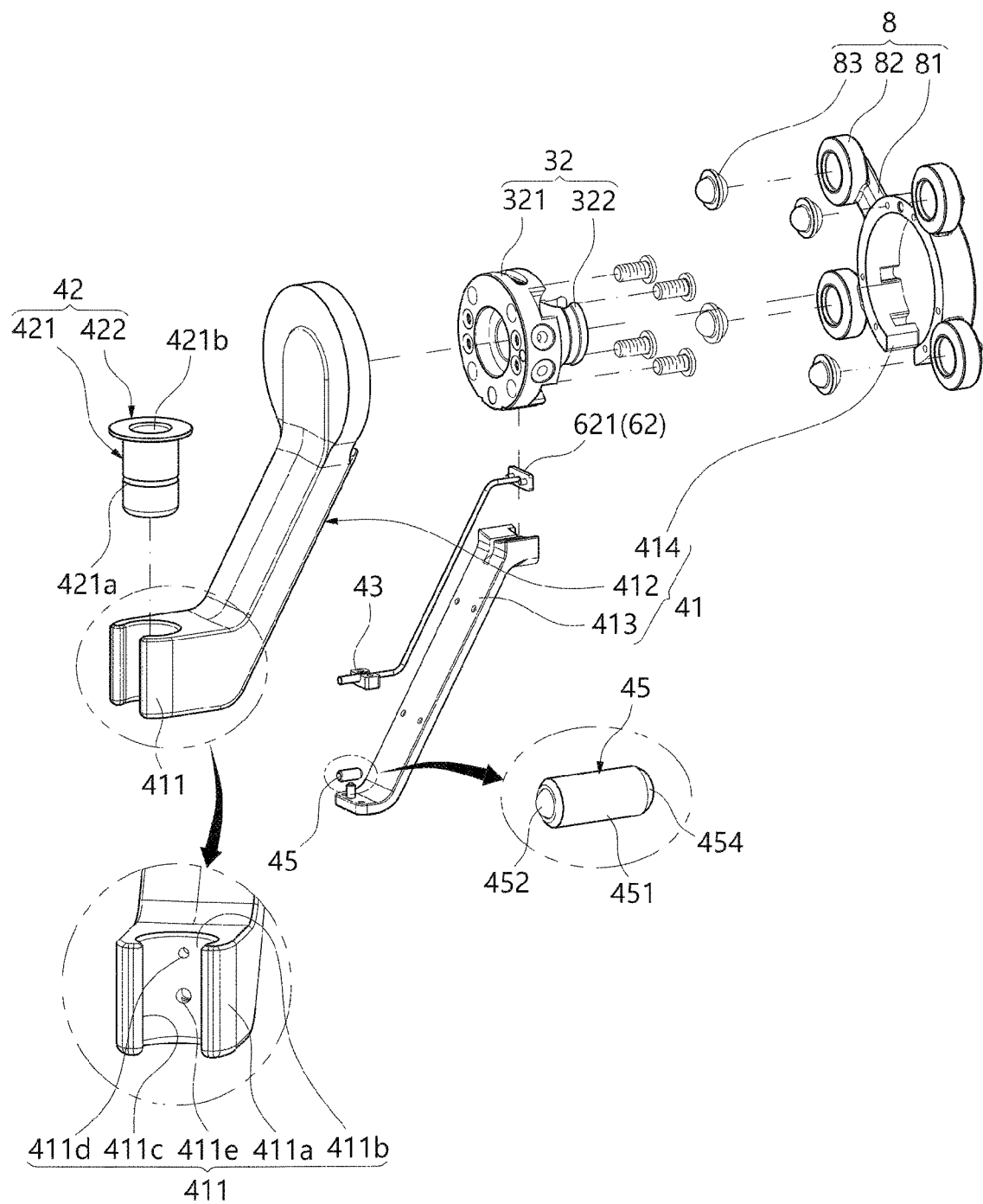
FIG. 8 is an exploded perspective view of a tool mounting unit in an end effector of a surgical robot according to an embodiment of the disclosure.

FIG. 8 is an exploded perspective view of a tool mounting unit in an end effector of a surgical robot according to an embodiment of the disclosure, and Referring to FIG. 8, the tool mounting unit 4 refers to an element to which a surgical tool for performing a surgical operation is mounted, which is detachably coupled to the end effector frame 2 by the clamping unit 3.

The tool mounting unit 4 includes a mounting bar 41 having a first end coupled to the end effector frame 2 and a second end formed with a tool supporter 411, a tool guide member 42 installed in the tool supporter 411 and supporting a surgical tool, and a tool presence detector 43 installed in the mounting bar 41 and configured to detect presence of the tool guide member 42.

The mounting bar 41 includes the tool supporter 411 formed at the lower end of the body shaped like a bar, a mounting bar body 412 formed with a detector accommodating groove to accommodate the tool presence detector 43 in the back of the tool supporter 411, a mounting bar cover 413 coupled to the mounting bar body 412 and including the second terminal 62, and a mounting bar coupler 414 coupled to an upper end of the mounting bar body 412 and installed with the second clamping unit 32 of the clamping unit 3.

The tool supporter 411 includes a supporting body 411a curvedly protruding from a lower end of the mounting bar body 412 in a horizontal direction, and a guide hole 411b formed to penetrate the supporting body 411a.

As shown in the enlarged part of FIG. 8, the supporting body 411a includes a sensor hole 411d to which a part of the tool presence detector 43 (to be described later) is fitted, and a stopper hole 411e to and through which a part of a guide member stopper 45 is fitted and exposed. The sensor hole 411d and the stopper hole 411e are formed on an inner circumferential surface of the guide hole 411b.

The guide hole 411b is formed in up and down directions and includes an opening 411c so as to allow the surgical tool to smoothly pass therethrough even in a state that a pedicle screw, the volume of which is larger than the diameter of the surgical tool, is installed in the surgical tool during a surgical operation. In this case, the gap of the opening 411c is smaller than the inner diameter of the guide hole 411b in order to prevent the inserted tool guide member 42 from separation.

The tool guide member 42 is approximately shaped like a bushing, is inserted in the guide hole 411b of the tool supporter 411, and includes an insertion portion 421 formed with a hanging groove 421a recessed on an outer surface of a cylindrical body formed with a tool insertion hole 421b, and a hanging ring 422 integrally formed on the top of the insertion portion 421 and settled and hung on the supporting body 411a.

Further, the tool guide member 42 may be made of metal, or may be structured to have a nonmetallic body coated with a metal layer.

The tool presence detector 43 is configured to detect the presence of the tool guide member 42. When the tool presence detector 43 detects the presence of the tool guide member 42, a controller for controlling the actuation of the surgical robot identifies that the surgical operation is proceeding, and stops the actuation of a robot arm, thereby preventing a medical accident that may occur as the robot arm moves during the surgical operation.

The tool presence detector 43 may include various kinds of sensors as long as it can detect the presence of the tool guide member 42. In this embodiment, the tool guide member 42 is made of metal, and a proximity sensor, which is called a metal detector, is provided to detect the installed state of the tool guide member 42.

Further, the tool supporter 411 adjacent to the tool presence detector 43 internally includes the guide member stopper 45 to elastically support the tool guide member 42 inserted in the guide hole 411b and prevent the tool guide member 42 from easy separation.

As shown in the enlarged part of FIG. 8, the guide member stopper 45 includes a ball housing 451 shaped like a tube, a ball 452 inserted in the ball housing 451, an elastic member (not shown) provided inside the ball housing 451 and applying elasticity to the ball 452, and a separation preventor 454 fastened to the ball housing 451, and is thus elastically settled in the hanging groove 421a of the tool guide member 42. Here, the separation preventor 454 is provided as a set screw.

The end effector of the surgical robot according to an embodiment of the disclosure includes a marker member 8 to provide an optical signal to an optical tracking system (not shown) in order to track a location of the end effector mounted to the robot arm.

There are no specific limits to the installation location, number, structure, etc. of marker members 8 as long as the marker members 8 can readily transfer an optical signal to the optical tracking system. However, according to this embodiment, four marker members 8 are equiangularly installed at the outer side of the mounting bar coupler 414.

Further, the marker member 8 includes a marker rod 81 integrally formed in the mounting bar coupler 414, a marker accommodator 82 formed at the end of the marker rod 81 and including a marker groove, and a marker 83 inserted and installed in the marker accommodator 82.

Here, the marker 83 is to provide reflected light to the optical tracking system (OTS) and obtain location information through a calculation process, and is achieved by a publicly-known common marker.

Below, the operations of the end effector of the surgical robot according to an embodiment of the disclosure will be described in brief.

Figure 9A:
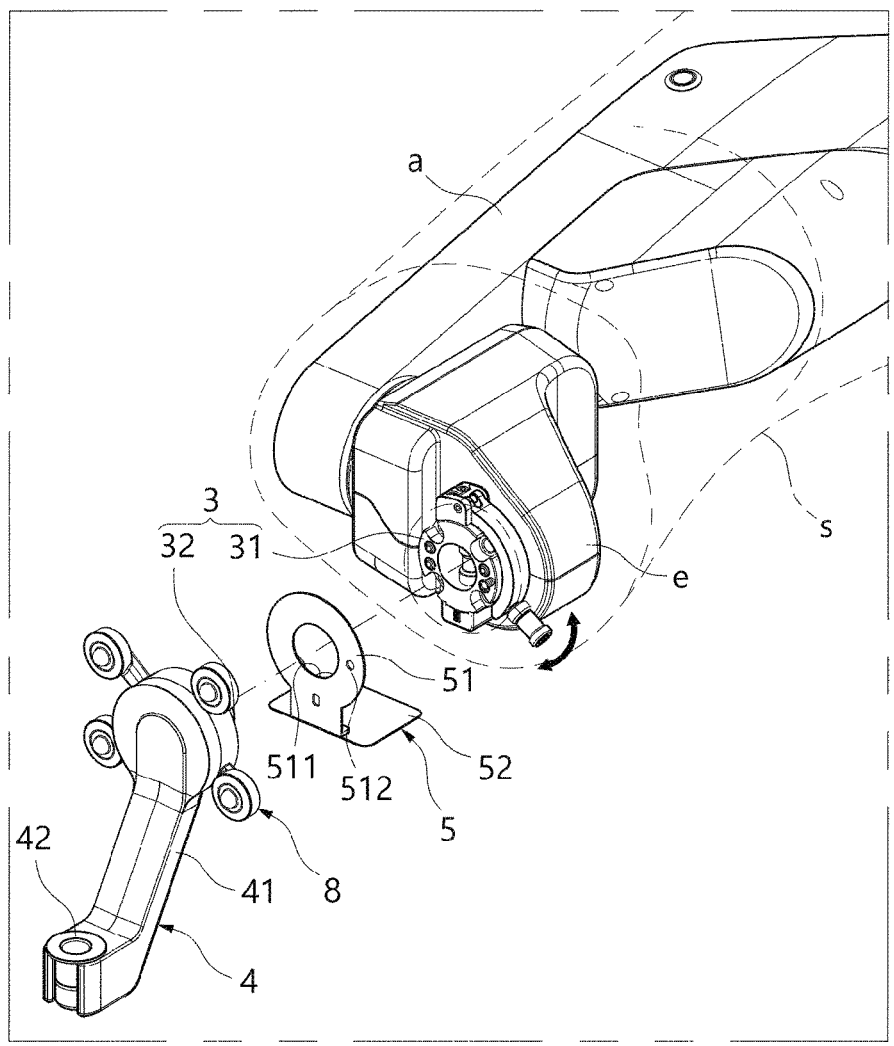
Figure 9B:
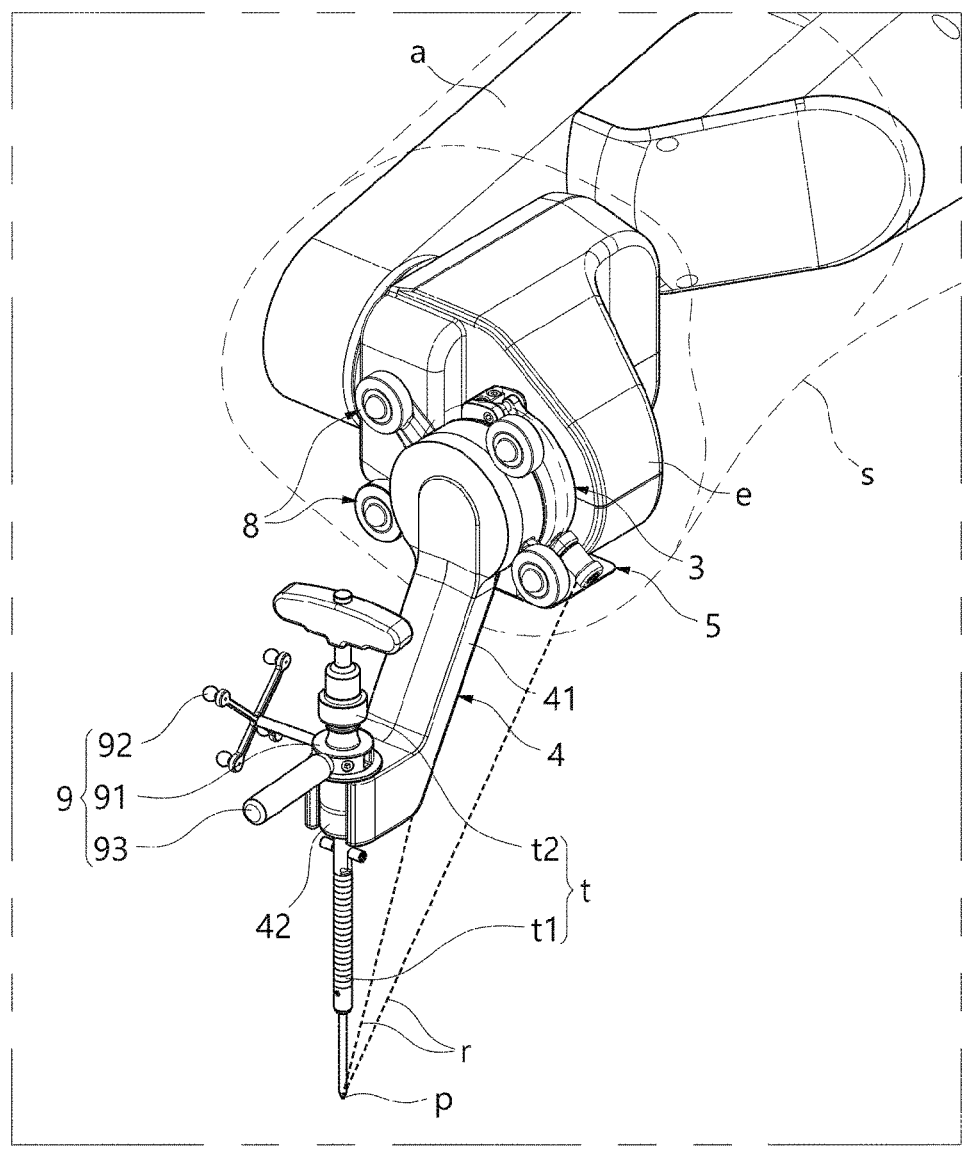
Figure 9C:
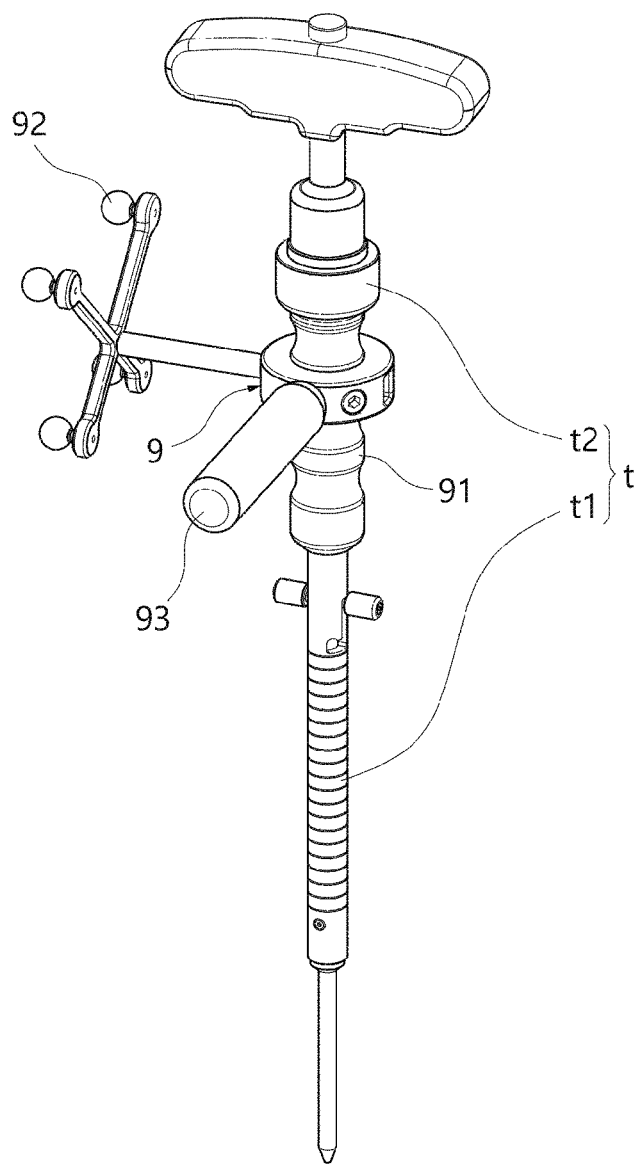

FIGS. 9A to 9C are views for describing operations of an end effector of a surgical robot according to an embodiment of the disclosure, in which FIG. 9A shows a state before the tool mounting unit is mounted, FIG. 9B shows a state that a sterilized cloth and a tool mounting unit are installed and a surgical tool is installed, and FIG. 9C is a perspective view of the surgical tool used in a pedicle screw insertion surgery, which is one of representative spine surgeries.

As shown in FIG. 9A, the force/torque sensor module 1 is coupled to the sensor module mounting portion 21, the force/torque sensor module 1 is installed at the end of the robot arm a, the first clamping unit 31 is coupled to the clamp mounting portion 22, and the line laser 7 is coupled to the laser bracket 25, and the end effector case 23 is assembled by means of the case holding bracket 24.

In this state, the end effector e including the robot arm is covered with the sterilized cloth s provided as vinyl paper or the like, the drape adapter 5 is inserted in a portion of the first clamping unit 31, the second clamping unit 32 installed in the tool mounting unit 4 is inserted in the first clamping unit 31, and a locking operation is performed, thereby mounting the tool mounting unit 4.

Below, the process of coupling the second clamping unit 32 to the first clamping unit 31 will be described in more detail. When the closing operation of the clamp lever 312 is performed in the state that the locking hole of the clamp projection 322 of the second clamping unit 32 is put on and fitted to a portion of the clamping shaft 313 having a small outer diameter while the clamp lever 312 is opened, the locking projection of the clamping shaft 313 is fitted and locked to the locking hole.

After the tool mounting unit 4 is mounted to the end effector frame 2 as described above, the tool guide member 42 is inserted in the tool supporter 411 of the mounting bar 41, and a surgical-tool handle device 9 installed with the surgical tool t is inserted and supported in the tool guide member 42.

Here, the surgical-tool handle device 9 includes a handle body 91, a surgical-tool marker member 92, and a grip member 93.

In a case where the foregoing surgical-tool handle device 9 is used in a surgical operation, a user can control the surgical tool t with one hand while gripping the grip member 93 with the other hand, and it is thus possible to accurately perform the surgical operation by preventing the location of the surgical-tool marker member 92 from being changed even though the surgical tool t moves.

In more detail, the surgical-tool marker member 92 is not rotatable as fixed to the handle body 91, so that the reflected light can be provided to the optical tracking system (OTS) while keeping a state of facing the optical tracking system, thereby continuously and accurately obtaining location information such as an endpoint location of the surgical tool, etc. based on a calculation process.

Further, there are no limits to the kinds or shapes of the surgical tool t. For example, the surgical tool t according to this embodiment includes a medical screw surgical device t1 that performs a reaming process and a tapping process with regard to a pedicle, and a process of inserting a pedicle screw into the pedicle during the pedicle screw insertion surgery, and a control tool t2 connected to an upper portion of the medical screw surgical device t1 in order to control the medical screw surgical device t1.

When the surgical tool t is mounted to the tool mounting unit 4 as described above, the robot arm is actuated by a given actuation signal to move a surgical location. In this case, the line laser 7 is actuated to emit a laser beam, and the laser beam r forms an intersection of marking a surgical site while passing through one pair of obliquely formed beam emission slits 233 as shown in FIG. 9B, thereby putting the lower end of the surgical tool t in position and safely and easily performing the surgical operation while checking an accurate surgical site.

Although the features and operations of the end effector of the surgical robot according to the embodiments of the disclosure have been described above, these are for illustrative purposes only, and it is understood by a person having ordinary knowledge in the art that change or replacement can be made in the foregoing embodiments of the disclosure without departing from technical scope of the disclosure.

Therefore, it is appreciated that the scope of the disclosure falls within the appended claims and its equivalents.

INDUSTRIAL APPLICABILITY

The end effector of the surgical robot according to the disclosure can rapidly and conveniently perform a surgical operation by the robot to thereby not only safely carry out a surgical process but also easily and accurately grip a surgical tool during the surgical operation and set and keep a location of the surgical tool and a surgical site, and can be installed and used as the end effect in the arm of the surgical robot.

The invention claimed is:

1. An end effector of a surgical robot, comprising:
   a force/torque sensor assembly configured to be mounted to a robot arm of the surgical robot to measure external force applied to the end effector and control operation of the surgical robot;
   an end effector frame to which the force/torque sensor assembly is coupled;
   a clamping assembly disposed in the end effector frame;
   a tool mounting unit having a bar-shaped body and configured to be detachably coupled to the end effector frame to support a surgical tool;
   an end effector case surrounding an outside of the end effector frame; and
   a line laser disposed in the end effector frame and configured for generating a laser beam for marking a surgical site,
   wherein the clamping assembly comprises a first clamping assembly configured to be installed in the end effector frame, and a second clamping assembly configured to be installed in the tool mounting unit and detachably coupled to the first clamping assembly,
   wherein the end effector further comprises a drape adapter disposed between the end effector frame and the tool mounting unit to hold a sterilized cloth,
   wherein the end effector frame comprises a sensor module mounting frame to which the force/torque sensor assembly is mounted, a clamp mounting frame to which the first clamping assembly is mounted, and a case holding bracket to which the end effector case is coupled,
   wherein the end effector case comprises a pair of beam emission slits formed to allow the laser beam generated by the line laser to be directed to an outside of the end effector case, and
   wherein the drape adapter comprises:
   a sterilized cloth holding plate interposed between the end effector frame and the tool mounting unit and configured for holding the sterilized cloth, and
   a light transmissive plate connected to the sterilized cloth holding plate and facing the pair of beam emission slits.

2. The end effector of the surgical robot of claim 1, wherein the tool mounting unit comprises:
   a mounting bar having a first end connected to the end effector frame and a second end opposite to the first end;
   a tool guide member having a cylindrical body and configured to be detachably coupled to the second end of the mounting bar to support the surgical tool; and
   a tool presence detector disposed in the mounting bar and configured to detect presence of the tool guide member.

3. The end effector of the surgical robot of claim 2, wherein the second end of the mounting bar comprises a supporting body curvedly formed in a lower portion of the mounting bar body, a guide hole formed through the supporting body, and an opening formed at one side of the supporting body.

4. The end effector of the surgical robot of claim 3, wherein the mounting bar comprises:
   a mounting bar body accommodating the tool presence detector; and
   a mounting bar cover coupled to the mounting bar body and including a second terminal configured to be connected to a first terminal disposed in the end effector frame.

5. The end effector of the surgical robot of claim 1, further comprising a marker disposed on the tool mounting unit and configured to provide an optical signal to an optical tracking system to track a location of the end effector.

6. The end effector of the surgical robot of claim 3, wherein the tool guide member comprises:
   a cylindrical insertion body configured to be inserted into the guide hole and having a hanging groove recessed on an outer surface thereof; and
   a hanging ring disposed on an upper end of the cylindrical insertion body such that the hanging ring is hung on the supporting body when the cylindrical insertion body is inserted into the guide hole.

7. The end effector of the surgical robot of claim 6, wherein the mounting bar further includes a guide member stopper disposed in the mounting bar body, the guide member stopper being configured to be elastically seated in the hanging groove.

* * * * *